(12) United States Patent
Jaccard

(10) Patent No.: US 7,765,619 B2
(45) Date of Patent: Aug. 3, 2010

(54) CORSET

(75) Inventor: Jean-Patrick Jaccard, Caslano (CH)

(73) Assignee: Sports & Supports Limited, Dublin (IE)

( * ) Notice: Subject to any disclaimer, the term of this patent is extended or adjusted under 35 U.S.C. 154(b) by 223 days.

(21) Appl. No.: 11/914,359

(22) PCT Filed: Apr. 4, 2006

(86) PCT No.: PCT/EP2006/003043

§ 371 (c)(1),
(2), (4) Date: Nov. 13, 2007

(87) PCT Pub. No.: WO2006/119827

PCT Pub. Date: Nov. 16, 2006

(65) Prior Publication Data

US 2008/0171955 A1    Jul. 17, 2008

(30) Foreign Application Priority Data

May 10, 2005   (IT) .......................... MI2005A0835

(51) Int. Cl.
*A41F 19/00*    (2006.01)
(52) U.S. Cl. ......................... 2/310; 128/99.1
(58) Field of Classification Search .................. 2/44, 2/46, 48, 50–51, 92, 102, 69, 310–317, 338; 128/99.1, 100.1, 101.1, 102.1
See application file for complete search history.

(56) References Cited

U.S. PATENT DOCUMENTS

| 4,175,553 | A | * | 11/1979 | Rosenberg ................... 602/19 |
| 4,794,916 | A | | 1/1989 | Porterfield et al. |
| 5,040,524 | A | * | 8/1991 | Votel et al. ................... 602/19 |
| 5,188,585 | A | | 2/1993 | Peters |
| 6,425,876 | B1 | | 7/2002 | Frangi et al. |
| 7,426,754 | B2 | * | 9/2008 | Chun et al. ...................... 2/46 |
| 7,473,235 | B2 | * | 1/2009 | Schwenn et al. .............. 602/16 |

FOREIGN PATENT DOCUMENTS

| EP | 0 368 583 A | 5/1990 |
| EP | 1 084 634 A1 | 3/2001 |
| GB | 410 430 A | 5/1934 |

OTHER PUBLICATIONS

International Search Report of PCT/EP2006/003043 filed Apr. 4, 2006, date of mailing Aug. 1, 2006.

\* cited by examiner

*Primary Examiner*—Tejash Patel
(74) *Attorney, Agent, or Firm*—Young & Thompson

(57) ABSTRACT

A corset (100) includes a first portion (5) and a second portion (5') with substantially the same shape as the first portion (5). Each portion (5, 5') includes a solid band (50) and a plurality of laces (52) which protrude from one end of the solid band (50). The two portions (5, 5') are constrained to each other by crossing the laces (52) with each other and by closing the ends of groups of laces by closure elements (56). The closure elements (56) of the laces are connected to tightening members (6) which can be operated manually by the user to tighten the laces (52).

10 Claims, 4 Drawing Sheets

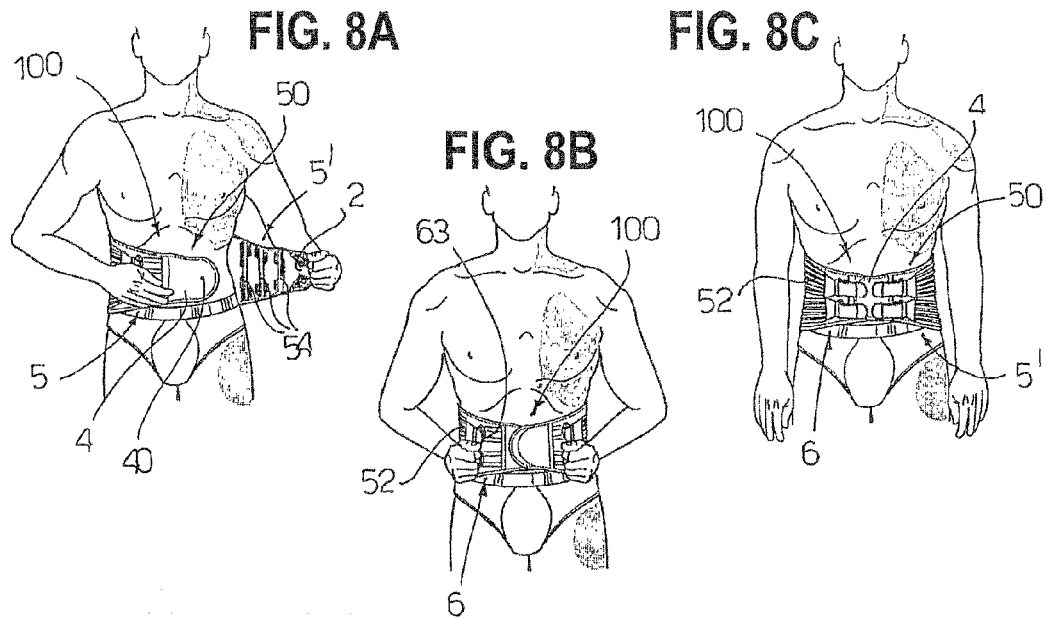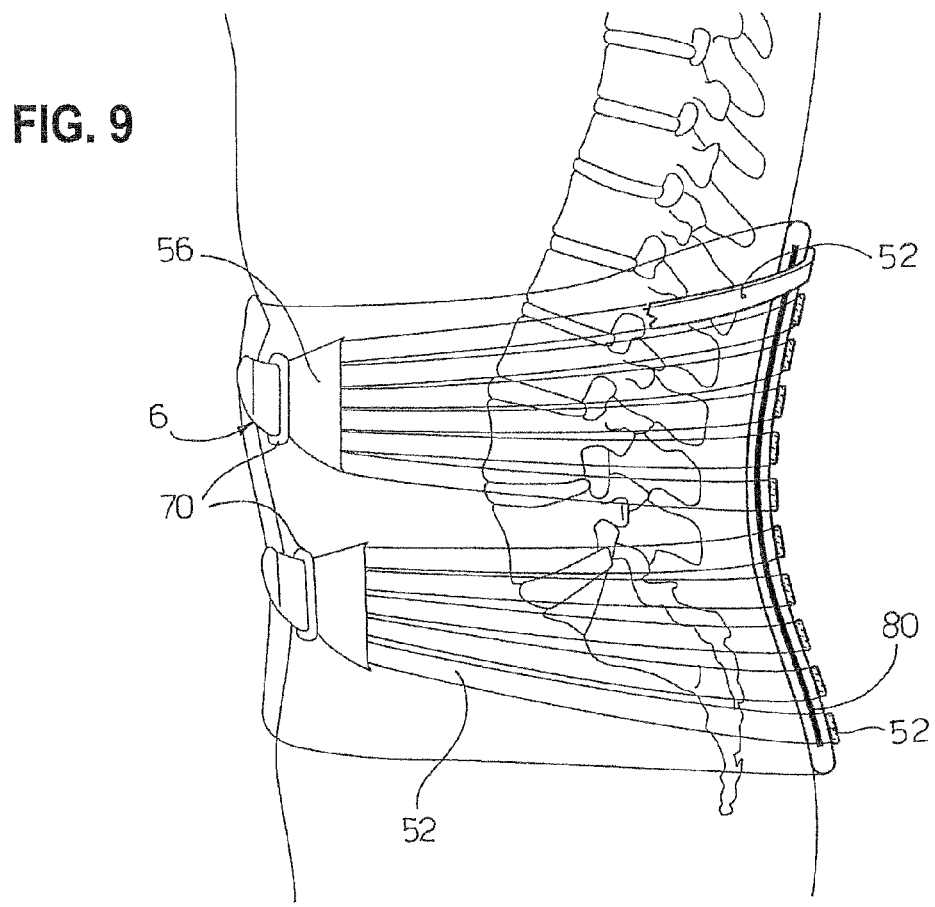

CORSET

The present invention refers to the field of the articles for health and orthopaedic use for rehabilitation and for prevention of injuries and in particular to a joint support, such as a corset.

As is known, a corset comprises an elastic band which surrounds the patient's lumbar and abdominal region to protect the lower part of the spine and maintain it in the correct position.

Patent application PCT WO99/66869 describes a corset which comprises a main band which has at one end Velcro handles designed to be anchored on the other end part of the main band to close the corset in a tubular configuration round the user's waist. The main band is provided with a rear central portion made of a very elastic material.

Fabric laces which cross over each other passing over the central elastic portion are connected to the main band. Velcro handles designed to be fixed to the main band to further tighten the corset on the user's waist are provided at the ends of the laces.

This type of corset presents some drawbacks due above all to the difficulty in fitting it, particularly for those people who have impaired mobility.

In fact, during the first stage of closure of the elastic band, a substantial effort is required of the patient, necessary to extend the rear central elastic part of the band.

In the second stage of closure of the laces, on the other hand, the user has a certain difficulty in finding the Velcro handles of the laces with his hands, because some stout patients have difficulty in seeing the sides of their pelvis.

It must be considered that during the first stage of closure of the band, if the central elastic part were not extended correctly, on pulling the laces in the second stage the central elastic part would pucker causing aesthetic and functional defects of the corset.

The object of the present invention is to eliminate the drawbacks of the prior art, providing a corset that is versatile, practical for the user and at the same time cheap and simple to make.

These objects are achieved in accordance with the invention with the corset whose characteristics are listed in appended independent claim 1.

Advantageous embodiments of the invention are apparent from the dependent claims.

The corset according to the invention comprises a first portion and a second portion with substantially the same shape as the first portion. Each portion of the corset comprises a solid band and a plurality of laces which protrude from one end of the solid band. The laces of the first portion are crossed with the laces of the second portion and the ends of groups of laces are closed by closure means so as to constrain the two portions of the corset to one another.

The closure means of the laces are connected to tensioning means which can be operated manually by the user to tighten the laces and to allow a further closure of the corset.

Further characteristics of the invention will be made clearer by the detailed description that follows, referring to a purely exemplary and therefore non limiting embodiment thereof, illustrated in the appended drawings, in which.

FIGS. 8A, 8B, and 8C are three front views illustrating the three successive stages for fitting of the corset according to the invention on the user; and FIG. 9 is a partially sectional side view illustrating the corset according to the invention worn by a user in the upright position, in which the action thereof on the lower vertebrae of the spine is shown.

Figure 4:
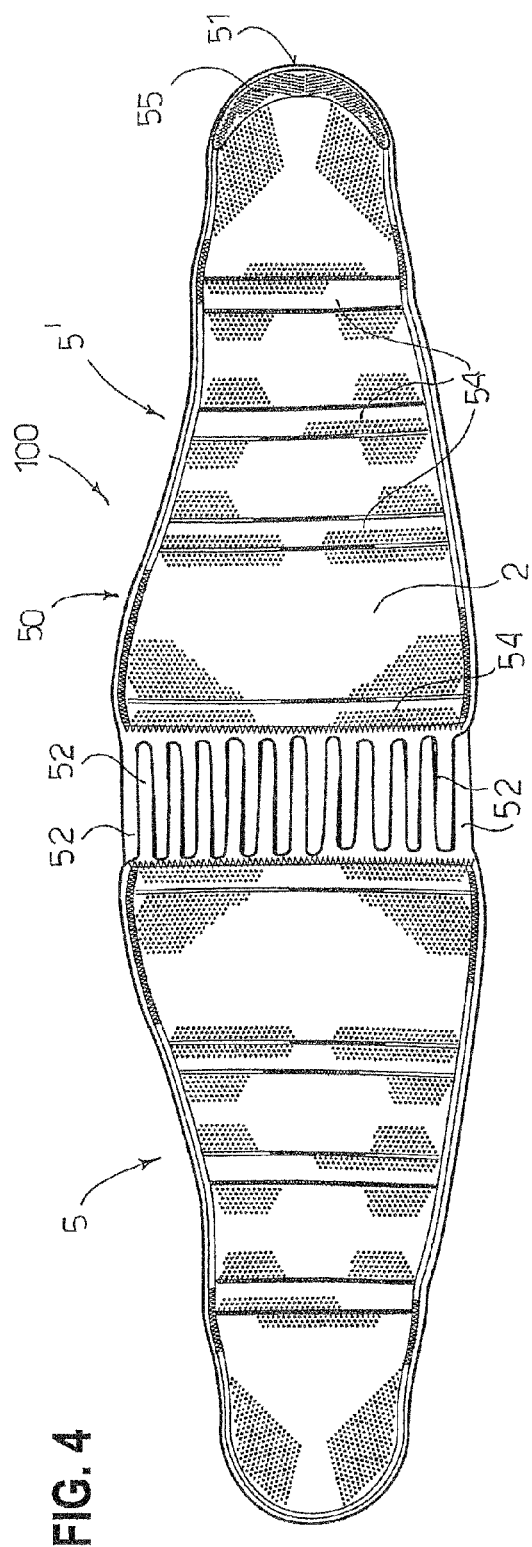
FIG. 4 is a plan view of the corset according to the invention in a spread-out position and taken from the bottom surface destined to face towards the user's body.
Figure 5:
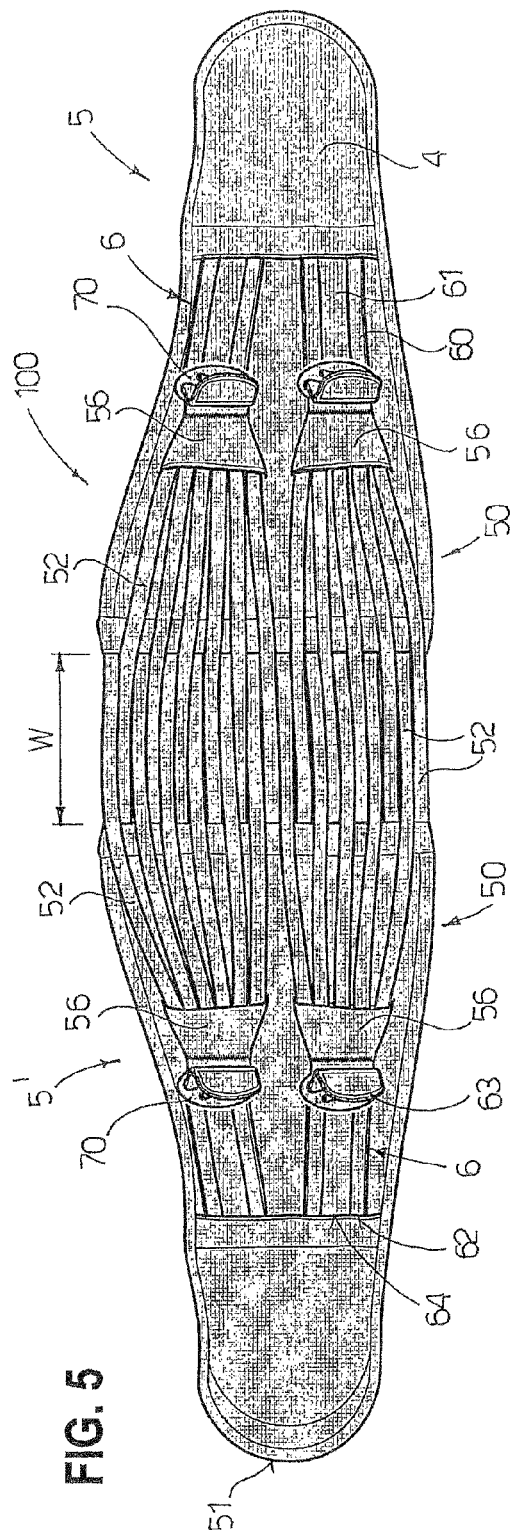
FIG. 5 is a plan view of the corset of FIG. 4 taken from the top surface destined to face outwards.

The corset according to the invention, denoted as a whole with reference numeral 100 and illustrated as a whole in FIGS. 4 and 5, is described with reference to the figures.

Figure 1:
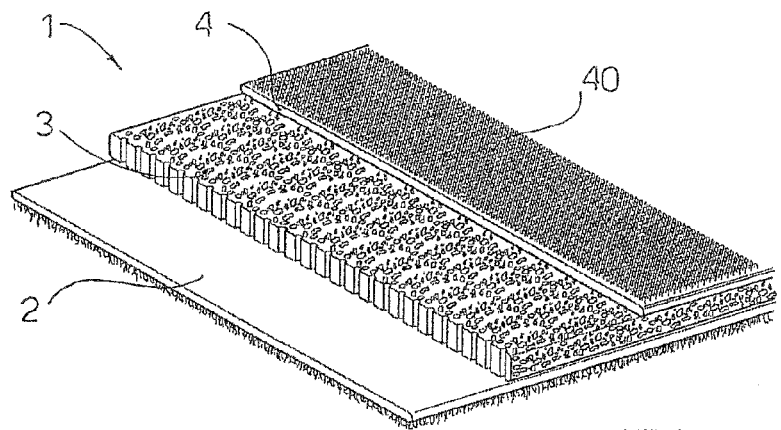
FIG. 1 is a perspective, partially broken off, cross-sectional view, illustrating a multilayer sheet used to make the corset according to the invention.

Realization of the corset 100 starts from a flat multilayer sheet 1, as shown in FIG. 1. The multilayer sheet 1 comprises:

a bottom layer 2 destined to go towards the user's body,
a middle layer of padding 3, and
a top layer 4 destined to face outwards.

The bottom layer 2, being in contact with the skin, must be made of an anallergic breathable material.

The middle layer 3 must be made of a cushioning breathable material, such as, for example, an open-cell plastic material like polyurethane (PU).

The upper layer 4 must have an upper surface 40 suitable for Velcro-type coupling. Therefore, the upper surface 40 of the top layer 4 has a plurality of loops able to couple, in an anchoring relationship, with a plurality of matching hooks of a Velcro-type anchoring element, as will be described below.

For this purpose the top layer 4 can be made of nylon fabric, suitably treated, so as to obtain an upper surface 40 with a plurality of loops.

The multilayer sheet 1 preferably is obtained by flame bonding. That is to say, the bottom layer 2 and the middle layer 3 are fed from two respective rolls. The middle layer 3 is made to pass near a flame which heats it on the side facing the bottom layer 2 to allow bonding thereof. Then the two layers 2 and 3 are made to pass through a calender which carries out the bonding. The outer side of the middle layer 3 is subsequently flame heated and bonded by means of a calender with the top layer 4 fed from a roll.

The middle layer 3 made of PU allows good adhesion to the bottom layer 2 and to the top layer 4, through flame bonding. Flame bonding is an example of the types of bonding between materials that can be carried out; alternatively there are other methods such as spread or sprayed glues, hot glues, etc.

The multilayer sheet 1, substantially rectangular in shape, is fed to a blanking machine. The multilayer sheet 1 is then compressed between two die halves which perform blanking along a pre-established outline, so as to obtain a first portion of corset, as shown in FIGS. 2 and 3.

The portion of corset 5 comprises a solid band 50, substantially trapezoid or tapered in shape, decreasing in size towards a rounded end 51. A plurality of laces 52 shaped like rectangular strips protrude from the distal end with respect to the rounded end 51 of the band 50. The laces 52 are of the same length and width and are disposed equidistant from each other so as to define a plurality of spaces 53 of such a width as to be able to receive the laces 52 of another portion of corset. To be exact, eleven laces 52 are provided on the portion of corset 5.

Figure 2:
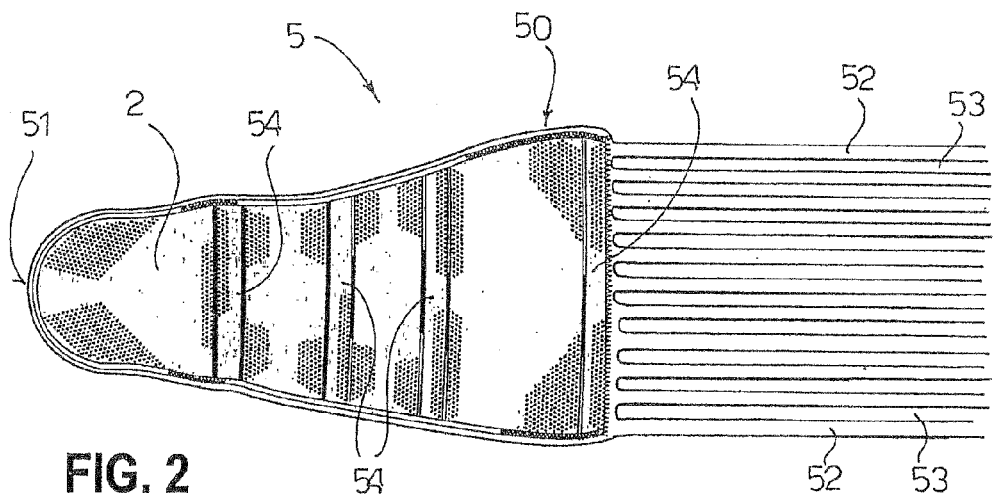
FIG. 2 is a plan view illustrating a portion of the corset according to the invention taken from the bottom surface destined to face toward the user's body.

With reference to FIG. 2, reinforcing strips 54 disposed crosswise with respect to the laces 52 are sewn on the bottom layer 2 of the band 50. The reinforcing strips 54 form pockets able to receive metal or stiff plastic inserts in the form of rods to stiffen the corset. By way of example, four reinforcing strips 54 disposed in a rear or in a lateral position and suitably spaced apart from each other are provided.

Figure 3:
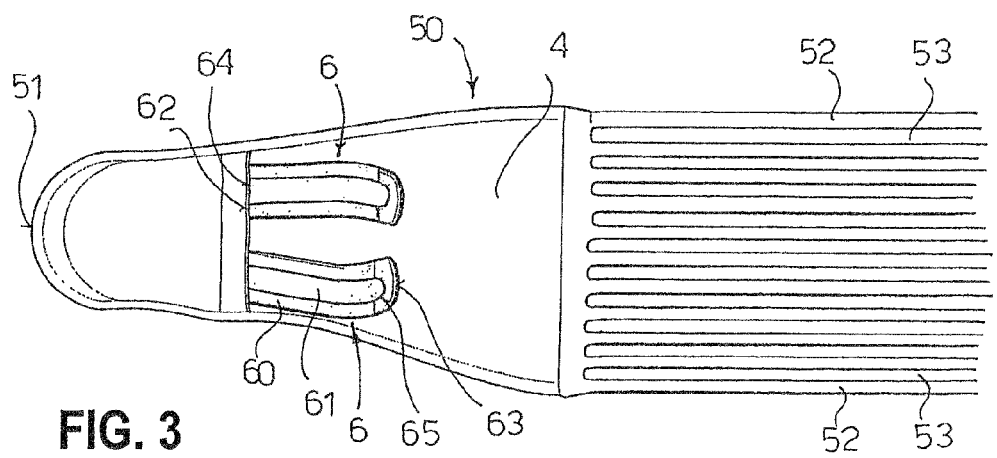
FIG. 3 is a plan view illustrating the portion of corset of FIG. 2 taken from the top surface destined to face outwards.

With reference to FIG. 3, two double straps 6 made of the same material as the top layer 4 are provided on the top layer 4 of the band 50. The straps 6 extend in the same direction as the laces 52, in an intermediate position of the band 50. Each double strap 6 comprises a main strip 60 and a secondary strip 61 superimposed on the main strip 60. The main strip 60 has a greater width and length and is stiffer with respect to the secondary strip 61.

The main strip 60 and the secondary strip 61 are fixed to the top layer 4 of the band 50, by sewing to one of their respective ends 62, 64. The other ends 63 and 65 of the main strip 60 and of the secondary strip 61, on the other hand, are free. In the portion near its free end 63, the main strip 60 has hook-type anchoring elements 66 designed to engage in an anchoring relationship with the loops 40 which make up the top layer 4 of the solid band 50 and of the straps 6.

As shown in FIGS. 4 and 5, in order to make the corset 100, a second portion of corset 5' is made, substantially the same as the first portion of corset 5, in which like elements are indicated with the same reference numerals.

As shown in FIG. 4, in the bottom layer 2 of the second portion of corset 5', near the rounded end 51 of the solid band 50, there is provided a strip of hook-type anchoring elements 55 designed to couple with the loop-type anchoring elements 40 of the top layer 4.

As shown in FIGS. 4 and 5, the laces 52 of one portion of corset 5 are inserted into the gaps 53 of the other portion of corset 5' and vice versa. Then, as shown in FIG. 5, the ends of the laces 52 are gathered into two groups of six laces and into two groups of five laces and are fixed, by sewing, to four closure strips 56 which are disposed in pairs near the straps 6 of the two portions of corset 5, 5'.

In this manner, the two portions of corset 5, 5' are constrained to each other, by crossing over of the laces 52 and cannot come apart from each other precisely because the ends of the laces 52 are fixed to the closure strips 56.

Figure 6:
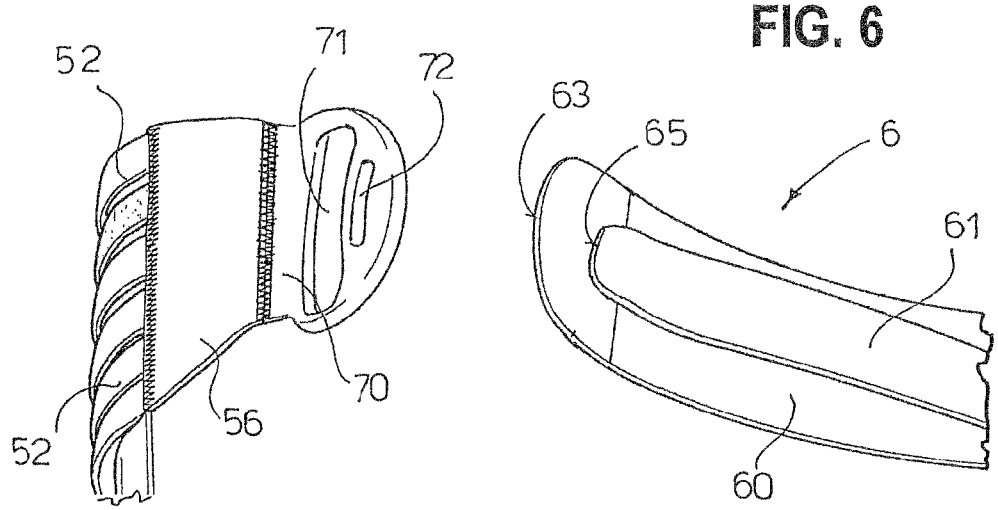
FIG. 6 is a perspective view, partially broken away, illustrating the closure system of the corset according to the invention, shown exploded.

As shown better in FIG. 6, a loop 70, made of a stiff material such as plastic, is fixed to each closure strip 56.

The loop 70 has a main hole 71, situated in a central position and a secondary hole 72 situated near the end of the loop 70 and smaller in size than the main hole 71.

Figure 7:
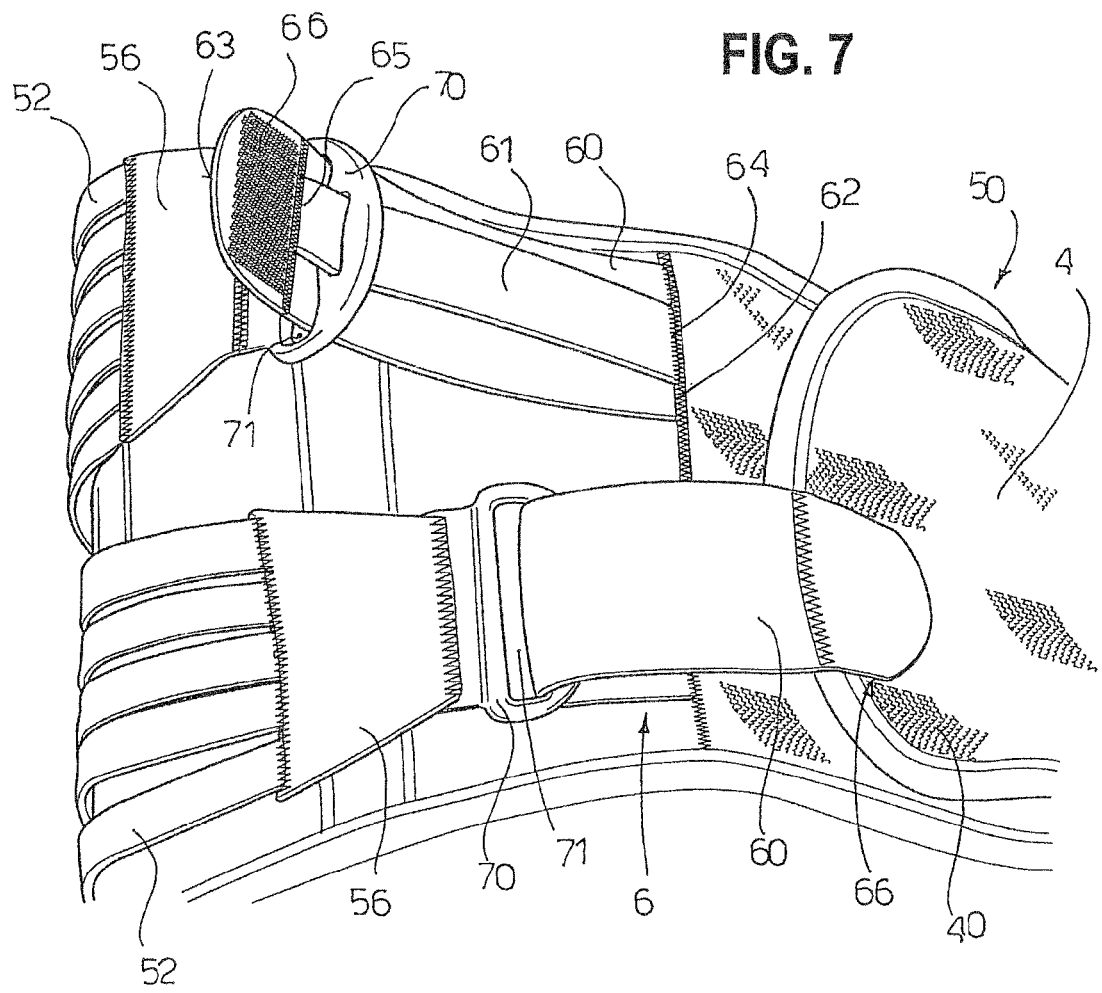
FIG. 7 is a perspective view illustrating the closure system of the corset assembled.

As shown in FIG. 7, the end 63 of the main strip 60 of the strap is inserted into the main hole 71 of the loop and the end 65 of the secondary strip 61 of the strap is inserted into the secondary hole 72 of the loop. Then, the end 65 of the secondary strip 61 is fixed, by sewing, to the main strip 60, near to the hook-type anchoring elements 66 disposed near the end 63 of the main strip.

At this point the corset 100 has been completed and is ready to be worn.

Since the secondary strip 61 of the strap is shorter, it bends the main strip 60 towards itself, so as to make the end portion 66 of the main strip protrude outward for an easier gripping by the user.

The strap 6 cannot be released from the loop 70, since the end 65 of the secondary strip 61 is fixed firmly to the primary strip 60. Thus the strap 6 behaves as a tightening element for the laces 52. In fact, sliding of the strip of the strap between the two ends 64 and 65 of the secondary strip 61 determines how far the laces 52 can extend during closure of the corset 100.

Furthermore, with reference to FIG. 5, the laces 52 of the two portions 5, 5' of corset are brought side by side at the rear of the corset forming a continuity of material, for a width W, when the corset is open and is spread out, that is to say the two bands 50 of the two portions of corset 5, 5' are spaced apart by a distance W covered by the side-by-side laces 52.

Clearly, when the corset 100 is worn and tightened by pulling the straps 6, the two bands 50 of the two portions of corset draw nearer to each other and the distance W is shortened.

The operation of fitting the corset on the user is described with reference to FIGS. 8A, 8B and 8C.

As shown in FIG. 8A, the user places the corset 100 around his/her waist with the bottom layer 2 facing his/her body, and the portion in which the laces 52 are arranged side by side disposed towards his/her back.

Then, as shown in FIG. 8B, the user closes the corset 100 to encircle his/her waist, anchoring the part with hook-type anchoring elements 55 provided on the bottom layer 2 at the end of the band of the second portion 5' of corset on the loop-type elements 40 provided on the top layer 4 of the band of the first portion 5 of corset. During this first stage it is sufficient to make the anchoring portion 55 of the band 50 adhere without applying traction.

Next, the user grips the ends 63 of the two opposite straps 6 and pulls them outward. As a result, the straps 6 slide in the respective loops 70 tightening the laces 52 and thus tightening the corset 100 around the user's waist.

As shown in FIG. 8C, once the desired tautness has been achieved, the user fixes the hook-type anchoring portion 66 of each strap 6 on the loops 40 of the top layer 4 of the band 50 of the second portion 5' of corset, so as to keep the laces 52 taut.

During the second stage of closure of the corset the patient will find on his/her sides the ends of the straps 6 which act as handles, already facing outward ready to be gripped, pulled and adjusted, without any need to look for them.

The corset 100 is formed by two portions 5, 5' joined at the back by the offset laces 52. In fact the rear part of the corset 100 is shaped like two large combs with long teeth offset from each other, so long as to surround outwardly the whole patient's torso and thus also the pockets 54 which contain the stiffening rods.

In this manner, as shown in FIG. 9, the stiffening rods 80, held on a large part of their surface by the laces 52, will remain close to the patient's body, obliged to perform their function of maintaining the patient's torso in the chosen position.

Numerous changes and modifications of detail within the reach of a person skilled in the art can be made to the present embodiment of the invention without thereby departing from the scope of the invention as set forth in the appended claims.

For example, even if two pairs of straps 60 are used as tightening means in the embodiment described, it is obvious that one pair of straps or a plurality of pairs of straps can be used, depending upon the height of the corset that is to be made.

The invention claimed is:

1. A corset (100) comprising:
a first portion (5); and
a second portion (5') with substantially the same shape as the first portion (5), each portion (5, 5') comprising a solid band (50) and a plurality of laces (52) which protrude from one end of said solid band (50), the laces (52) of the first portion (5) of the corset being crossed with the laces (52) of the second portion (5') of the corset, the ends of groups of said laces (52) being closed by closure means (56), so as to constrain to each other said two portions (5, 5') of the corset, wherein each said closure means (56) of the laces are connected to tightening means (6) which can be operated manually by the user to tighten said laces, and said laces (52) of the two portions (5, 5') of corset are brought side by side at the rear of the corset forming a continuity of material.

2. The corset (100) according to claim 1, wherein said solid bands (50) of the corset are provided with reinforcing strips (54) forming pockets able to receive stiffening roads (80) and in that in the rear part of the corset (100), said laces (52) are shaped like two large combs with long teeth offset from each other, so as to surround outwardly the whole patient's torso and thus also said pockets (54) which contain the stiffening rods (80).

3. The corset (100) according to claim 1, wherein said tightening means comprise a strap (6) which turns backwards through a loop (70) integral with said closure means (56) of the laces, said strap (6) having one end (62, 64) fixed to said solid band (50) and the other end (63) free to be able to be gripped and pulled by the user.

4. The corset (100) according to claim 1, wherein said closure means (56) comprise a strip (56) fixed to the ends of said groups of laces (52).

5. The corset (100) according to claim 3, wherein said strap (6) comprises a main strip (60) and a secondary strip (61) smaller in width and length than the main strip, said secondary strip being superimposed on the main strip and having one end (64) connected near the free end (63) of the main strip, so as to force the free end (63) of the main strip to protrude outward.

6. The corset (100) according to claim 5 when it is dependent upon claim 3, wherein said loop (70) comprises a main hole (71) and a secondary hole (72) wherein said main strip (60) and said secondary strip (61) of the strap, respectively, can slide.

7. The corset (100) according to claim 3, wherein near said free end (63) of the strap (6) there are provided Velcro type anchoring means (66) able to engage in an anchoring relationship with complementary anchoring means (40) provided on the outward facing layer (4) of said solid band (50) of the corset or on said strap (6).

8. The corset (100) according to claim 1, wherein said two portions (5, 5') of the corset are obtained by means of blanking starting from a bonded multilayer sheet (1).

9. The corset (100) according to claim 8, wherein said bonded multilayer sheet (1) comprises:

a bottom layer (2) destined to go towards the user's body, a middle layer of padding (3), and a top layer (4) destined to face outwards.

10. The corset (100) according to claim 9, wherein said bottom layer (2) is made of anallergic, breathable fabric, said middle layer (3) is made of an open-cell material such as polyurethane (PU), and said top layer (4) is made of a material, such as nylon, suitably treated to have a Velcro type anchoring surface (40).

\* \* \* \* \*